United States Patent [19]

Hara

[11] Patent Number: 4,600,884
[45] Date of Patent: Jul. 15, 1986

[54] APPARATUS FOR DETERMINING THE CONTINUITY OF HOLES FORMED IN A CONDUCTIVE SHEET

[75] Inventor: Akio Hara, Tokyo, Japan

[73] Assignee: Toyo Seikan Kaisha Ltd., Tokyo, Japan

[21] Appl. No.: 416,091

[22] Filed: Sep. 8, 1982

[30] Foreign Application Priority Data

Sep. 8, 1981 [JP] Japan .................................. 56-141221

[51] Int. Cl.⁴ ...................... G01N 27/12; G01R 33/12; G08B 21/00
[52] U.S. Cl. ...................................... 324/236; 331/65; 340/675
[58] Field of Search ............... 324/207, 208, 228, 236, 324/237, 234, 262; 331/65; 340/673-677

[56] References Cited

U.S. PATENT DOCUMENTS

| 3,742,477 | 6/1973 | Enabnit | 331/65 |
| 3,931,571 | 1/1976 | Hocking et al. | 324/236 |
| 4,270,088 | 5/1981 | Weischedel | 324/242 |

Primary Examiner—Reinhard J. Eisenzopf
Assistant Examiner—Walter E. Snow
Attorney, Agent, or Firm—Finnegan, Henderson, Farabow, Garrett & Dunner

[57] ABSTRACT

A method for detecting defective press punching, comprising steps of causing an electromagnetic sensor to approach a punched hole of a blank after products are punched by a press, and discriminating the quality of the punched products from the output level of the electromagnetic sensor that changes according to whether or not the circumference of the punched hole constitutes a closed loop electrically, and a device for performing the method.

5 Claims, 10 Drawing Figures

FIG.4(a)  FIG.4(b)
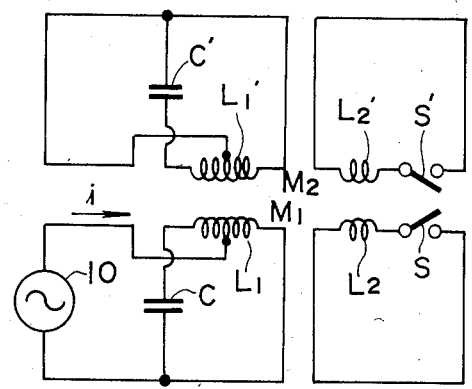
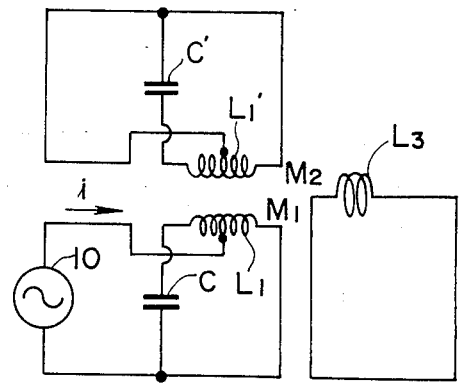
FIG.5
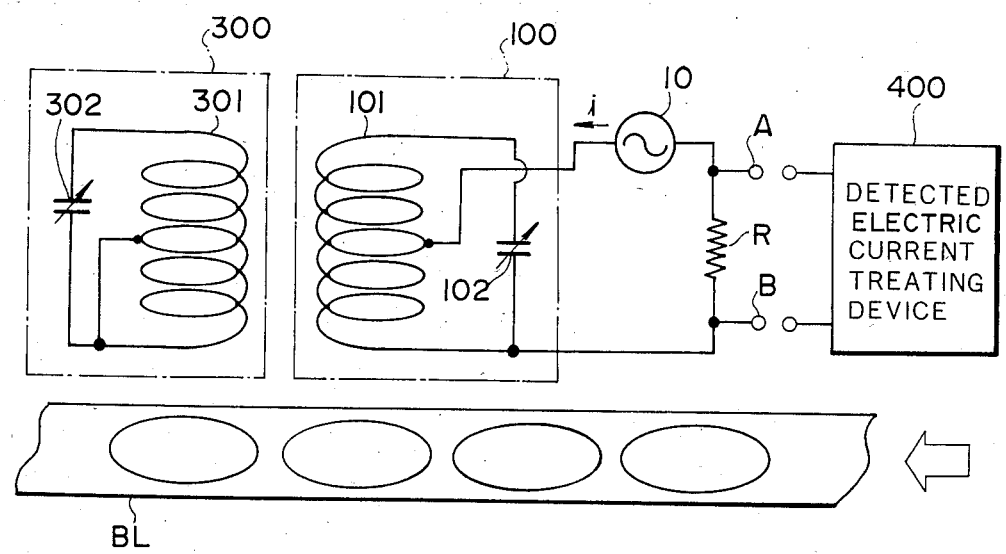

APPARATUS FOR DETERMINING THE CONTINUITY OF HOLES FORMED IN A CONDUCTIVE SHEET

BACKGROUND AND SUMMARY OF THE INVENTION

This invention relates to a method for detecting defective press punching and a device for performing the method, and more particularly to a method for detecting defective press punching through checking punched condition in a material after the punching is performed and a device for performing the method.

In general, in case of punching a product of a predetermined shape from a plate-shape material by a press, a dimensional interval of punching for each product should be limited to a minimum in order to effectively utilize the material to a maximum.

Now, if the feed speed of the material is changed due to some reasons or the material is smaller than a predetermined dimension, defects tend to occur in the punched product on the ground of superposed punched holes or overrun from the end portion of the material. The resulting defective product when used results in various inconveniences such as inability of fitting with other parts or inability of sealing the joined portions even though the fitting is achieved.

However, it is extremely difficult to accurately judge existence of the foregoing defects by monitoring or checking the shape of the punched product, and particularly, it is almost impossible to detect the minor defect on the end portion of the product to which both punching and bending processes are simultaneously applied.

This invention has been achieved in view of the foregoing actual circumstances, and its object is to provide a method for detecting defective punching of the press, in which defects on the end portion of the product punched by the press can be detected simply and accurately and to provide a device for performing the method.

According to this invention, a material after the product is punched by the press, hereinafter called "blanked material" or simply "blank", is monitored and whether or not the defect exists on the blank is electromagnetically detected, whereby the existence of the defect on the end portion of the product is judged.

Hereinbelow, the method for detecting the defective punching of the press and the device for performing the method according to this invention will be described in details by referring to the embodiments illustrated on the attached drawings.

BRIEF DESCRIPTION OF THE DRAWINGS

FIGS. 4(a) and 4(b) show another principle of the press punching defect detecting device according to this invention;

FIG. 5 is a schematic view showing an embodiment of the press punching defect detecting device constructed on the basis of the principle illustrated in FIG. 4.

DETAILED DESCRIPTION OF THE ILLUSTRATIVE EMBODIMENT

As required, a detailed illustrative embodiment of this invention is disclosed herein. The embodiment exemplifies this invention which may, of course, be embodied in various other forms, some of which may be radically different from the illustrative embodiment as disclosed.

However, the specific structural and functional details disclosed are representative and provide a basis for the claims herein which define the scope of this invention.

In the first place, the method for detecting defective press punching and the device for performing the method according to this invention will be described simply in the following.

Figure 1A:
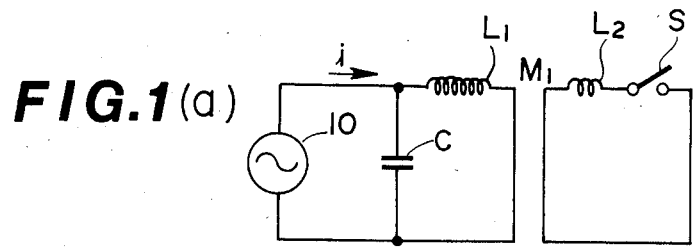
FIGS. 1(a) and 1(b) are circuitry diagrams showing a principle of the press punching defect detecting device according to this invention.

Referring initially to FIG. 1(a), a circuit constructed by an oscillator 10, coil $L_1$ and a capacitor C is a known parallel resonance circuit, and magnitude of an electric current i flowing in the circuit is greatly changed according to the inductance of the coil $L_1$ and the capacitance of the capacitor C.

Also, in the drawing, a circuit constructed by a coil $L_2$ and a switch S is a secondary circuit of the resonance circuit, and the coil $L_2$ and the coil $L_1$ of the resonance circuit are coupled by a mutual inductance $M_1$. Namely, a resonating condition of the resonance circuit in the condition where the switch S is off is determined by the inductance of the coil $L_1$ and the capacitance of the capacitor C, but a resonating condition of the resonance circuit in the condition where the switch S is turned on is determined by the mutual inductance $M_1$ of the coils $L_1$ and $L_2$ and the capacitance of the capacitor C.

Accordingly, in case that the inductance of the coil $L_1$ and the capacitance of the capacitor C are determined to allow the impedance of the resonance circuit to be a maximum when the switch S is turned off, namely, the value of the electric current i flowing in the resonance circuit to become a minimum (a maximum resonating condition), this resonating condition is collapsed when the switch S is turned on, and the value of the electric current i is greatly elevated.

Now, the blank punched by the press is discussed with respect to the secondary circuit. When a circumference of the punched hole (hereinafter referred to simply as a punched hole in the blank) is regarded as the coil of one turn, the hole portion produced after the punching corresponds to the coil $L_2$ of the secondary circuit, and whether or not there is the notch in the punched portion corresponds to whether or not the switch S of the secondary circuit is turned off or on.

Accordingly, in case that the coil $L_1$ of the resonance circuit is caused to approach whenever the punching of the material is carried out, the electric current i flowing in the resonance circuit is greatly changed depending on whether or not there is the notch in the punched portion, and when the mode of change of this electric current i is monitored, the existence of the notch at a punched hole of the blank, namely, the existence of the defect on the end portion of the punched product by the press can be detected.

Figure 1B:
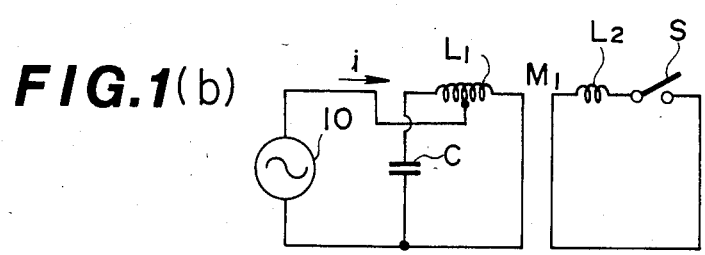

In case that the circuit shown in FIG. 1(b) in which the resistance loss of the coil $L_1$ is decreased is used, it is possible to obtain a remarkable change of the electric current.

Figure 2:
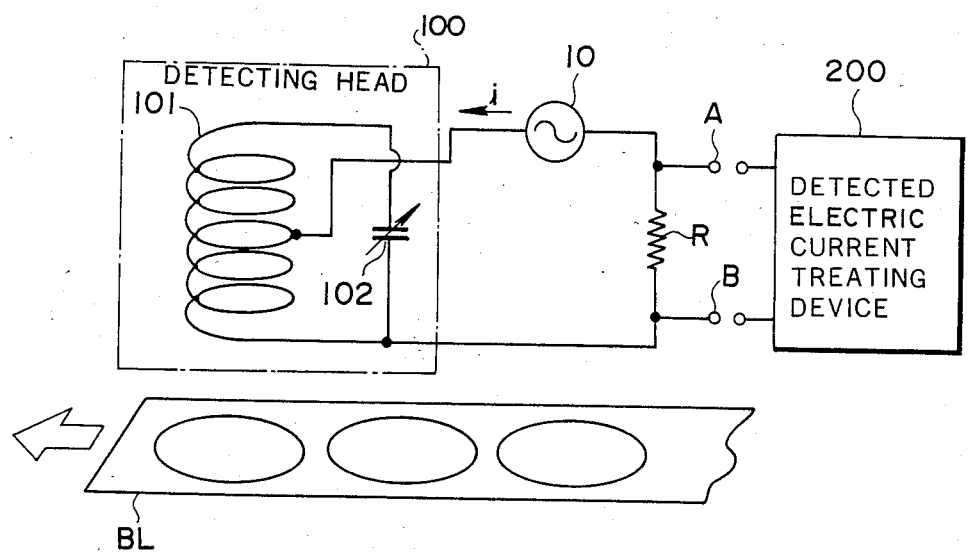
FIG. 2 is a schematic view of the embodiment of the press punching defect detecting device constructed on the basis of the principle illustrated in FIG. 1.

FIG. 2 exhibits one embodiment of the defective press punching detecting device according to this invention.

In the device of the embodiment, a detecting head 100 comprising a coil 101 and a variable capacitor 102 is properly disposed at an approached position of the punched hole of a blank BL shifting in the direction of an arrow from the press (not shown in the drawing), and whether or not there is a notch in the blank BL (refer to FIG. 1(b)) is detected. Namely, the parallel resonance circuit of the detecting head 100 is set at a maximum resonanting condition by a proper combination of the inductance of the coil 101 and the capacitance of the variable capacitor 102.

Then, an AC current i is supplied from the oscillator 10 to the detecting head 100, and the change of the electric current i is outputted from both terminals of a resistor R by means of terminals A and B.

Figure 3A:
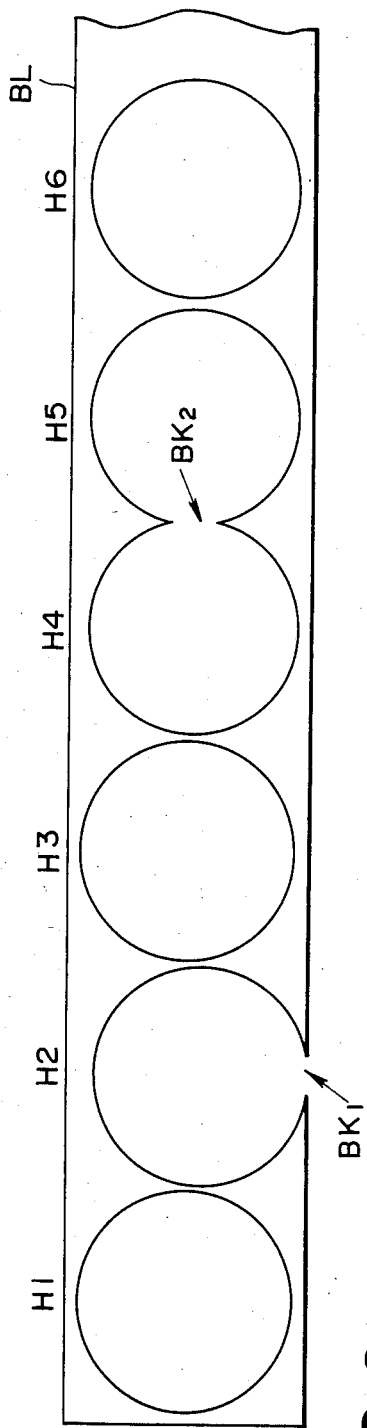
FIGS. 3(a) and 3(b) show an example of operations of the device of the embodiment illustrated in FIG. 2.
Figure 3B:
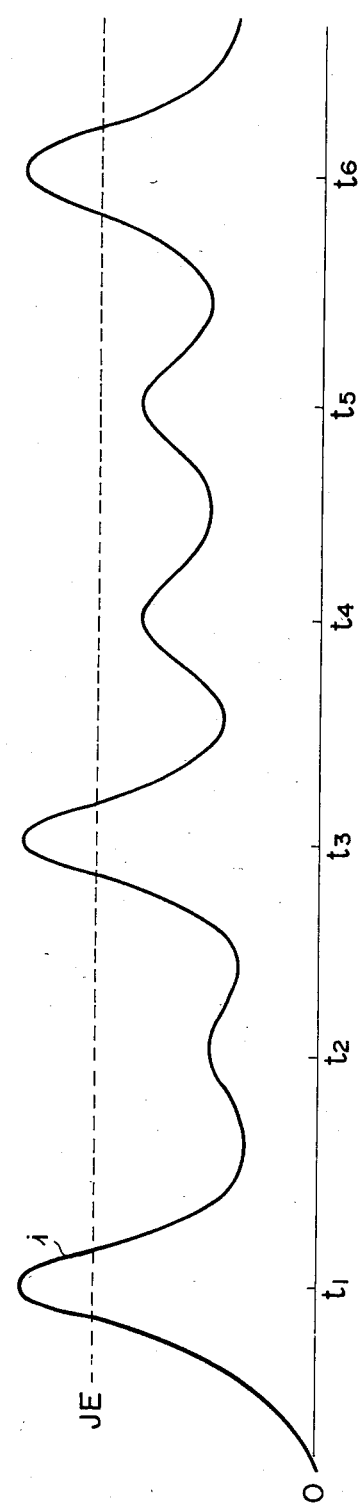

FIGS. 3(a) and 3(b) exhibit the mode of detection by the device of the embodiment of the existence of the notch in the blank BL (FIG. 2), and the operation of the device of the embodiment and the method for detecting defective punching are described in the following on the basis of the drawing.

It is assumed that two different kinds of the notches $BK_1$ and $BK_2$ occur in the detected blank BL as shown in FIG. 3(a).

FIG. 3(b) exhibits the mode of change of the electric current i (that is the output waveform across the terminals A and B after being shaped), and times $t_1$–$t_6$ are times when each punched portion $H_1$–$H_6$ of the blank BL shown in FIG. 3(a) is passed at the detecting head 100.

Accordingly, the operations of the device of the embodiment at each time $t_1$–$t_6$ are as follows:

at the time $t_1$: Since the punched portion $H_1$ is normal (forming closed loop), the mutual inductance exists between the punched portion $H_1$ and the coil 101 of the detecting head 100. With the existence of the mutual inductance, the resonating condition of the detecting head 100 is collapsed and the electric current i is increased.

at the time $t_2$: Since there is the notch $BK_1$ in the punched portion $H_2$, the secondary circuit (the punched portion $H_2$) becomes the open loop. Accordingly, the resonating condition of the detecting head 100 is maintained and the electric current i is decreased.

at the time $t_3$: Its condition is identical with the condition at the time $t_1$, and the electric current i is increased.

at the time $t_4$: Since there is the notch $BK_2$ between the punched portion $H_4$, the electric current i is decreased. In this case, the secondary circuit (the punched portion $H_4$) does not completely become an open loop because of the position of the notch $BK_2$, but the influence of the mutual inductance between the these punched portions $H_4$ and $H_5$ and the coil 101 of the detecting head 100 is small, and the resonating condition in the detecting head 100 is almost maintained. However, the electric current i is increased to some extent as compared with the condition at the time $t_2$.

at the time $t_5$: Its condition is identical with the condition at the time $t_4$, and the electric current i is maintained small.

at the time $t_6$: Its condition is identical with the condition at the times $t_1$ and $t_3$, and the electric current i is increased.

At the succeeding times, the electric current is outputted based on the conditions of the punched portion of the blank BL similar to the foregoing.

Accordingly, in case that a discriminating level JE is set for a detected electric current treating device 200 (FIG. 2) as shown in FIG. 3(b), and the electric current i exceeds the value of the discriminating level JE only when the punched portion by the press is normal, a defective punched portion can be easily detected. Further, the broad range of usages can be considered such that the detecting signal obtained by the detected electric current treating device 200 is used as emergency stop signal of the press or the various alarming signals.

The construction of the detecting head 100 is, of course, not limited to the embodiment shown in FIG. 2, and any constructions may be employed as long as the parallel resonating circuit is formed.

Also, the electric current supply means to the detecting head 100 and the electric current pick-up means, are not limited to the embodiment shown in FIG. 2, and any means can be employed as long as the detected mode is obtained at the detecting head 100, and can be outputted.

The description has been provided in the foregoing principle in which the detecting head 100 is constructed with the parallel resonating circuit from the easiness of embodying the concept into the device, but it is, of course, possible to use the series resonating circuit, and in this case, when there is the notch in the blank BL, the value of the electric current i is increased, and if punching is performed normally, the value of the electric current i is decreased. Furthermore, it is possible to use other electromagnetic inducing means for the detecting head 100. Namely, it is possible to use the unit to which the principle of the transformer is applied, and the unit with the ridge circuit by the coil may be used. That is, any means may be used as long as it can detect electromagnetically whether the punched portion is closed loop or open loop by regarding the punched portion of the blank BL as the coil of one turn.

In the foregoing, the embodiment of using the detecting head consisting of the parallel resonating circuit is described, but it is possible to provide the detecting head 100 and the dummy head 300 as shown in FIG. 5.

The FIGS. 4(a) and 4(b) are circuitry diagram for explanation of the operating principles of the case where the detecting head and the dummy head are provided.

As shown in FIG. 4(a), the dummy circuit is provided, which is constructed by the coil $L_1$, so wound as to emit the magnetic flux in the direction opposite to the direction of the coil $L_1$ of the parallel resonating circuit (hereinafter referred to as the basic resonating circuit) as shown in FIG. 1 and the capacitor C', and furthermore, the secondary circuit constructed by the coil $L_2'$ and the switch S' is provided. However, in FIG. 4(a), the basic resonance circuit constructed by the oscillator 10, coil $L_1$ and the capacitor C is constructed in such a way that the inductance of the coil $L_1$ and the capacitance of the capacitor C are set so that the maximum resonating condition is obtained when the switch S of the secondary circuit is turned off similar to the FIG. 1(a) or 1(b), and the corresponding dummy circuit is constructed in such a way that in case the oscillator 10 is assumed to be inserted for excitation (electric current may be separately supplied to the dummy circuit in the condition where the coil $L_1'$ of the dummy circuit emits the magnetic flux of the direction opposite to the direction of the magnetic flux emitted by the coil $L_1$ of the basic resonance circuit) when the switch $S'$ of the secondary circuit is turned off, so that the maximum resonating condition is produced. In case that the switches S and $S'$ of the secondary circuits of the circuits are turned on, the coil $L_1$ of the basic resonance circuit and the coil $L_2$ of the secondary circuit are coupled by the mutual inductance $M_1$, and the coil $L_1'$ of the dummy circuit and the coil $L_2'$ of the secondary circuit of the dummy circuit are coupled by the mutual inductance $M_2$.

When the foregoing circuit is considered with respect to the basic resonance circuit, and in case the switch S of the secondary circuit of the basic resonating circuit is turned off, the maximum resonating condition is retained so that the value of the electric current i becomes a minimum, and inversely, when the switch S is turned on, the mutual inductance $M_1$ is operated to collapse the resonating condition so that greatly increasing of the value of the electric current i is similar to that of the circuit described in the FIG. 1(a) or (b). Also, since the coil $L_1$ of the basic resonating circuit and the coil $L_1'$ of the dummy circuit are coupled by a predetermined mutual inductance, in case the basic resonance circuit is resonated, the dummy circuit also becomes the resonating condition, but since the secondary circuits are separately provided so that the operation of the dummy circuit does not spoil the fundamental operation of the foregoing basic resonance circuit.

In case the coils of the secondary circuits become a common coil $L_3$ as shown in FIG. 4(b) to form the closed loop, there occurs some difference in the mode of change of the electric current i.

In this case, when the secondary circuit becomes a closed loop, the mutual inductance $M_1$ for coupling the coil $L_3$ of the secondary coil and the coil $L_1$ of the basic resonance circuit tends to collapse the maximum resonating condition of the basic resonance circuit, but the mutual inductance $M_2$ for coupling the coil $L_3$ of the secondary circuit and the coil $L_1'$ of the dummy circuit which functions simultaneously with the foregoing operation works to cancel out the mutual inductance $M_1$ since the directions of the magnetic fluxes emitted by the coil $L_1$ and the coil $L_1'$ are opposite. Accordingly, the basic resonance circuit judges to assume that the secondary circuit is regarded as if the open loop by the provision of the dummy circuit, and reconstructs the maximum resonating condition. Namely, the value of the electric current i becomes a minimum.

The foregoing condition in the secondary circuit correponds to the case where the notch occurs by the superposition of the end portions of the two adjacent punched portions among the portions punched by the press.

Now, in the device of the embodiment shown in FIG. 5, the detecting head 100 constructed by the coil 101 and the variable capacitor 102 and a dummy head 300 constructed by a coil 301 and a variable capacitor 302 are properly disposed at positions approaching the punched portion of the blank BL which shift in the direction of arrow after being fed out from the press (not shown in the drawing), and detects whether or not there is the notch in the blank BL on the basis of the foregoing principle (refer to FIGS. 4(a) and (b)). Namely, the respective parallel resonance circuits of the detecting head 100 and the dummy head 300 correspond to the foregoing basic resonance circuit and the dummy circuit, and the setting is achieved to obtain the maximum resonating condition by the proper combination of the inductance of the coil 101, the capacitance of the variable capacitor 102, the inductance of the coil 301 and the variable capacitor 302 in case the identical power source is supplied.

In this device of the embodiment, the proper AC current i capable of obtaining the maximum resonating condition is supplied only to the detecting head 100 from the oscillator 10 (the parallel resonance circuit in the dummy head 300 is shortcircuited as shown in the drawing—provided that the electric current may be separately supplied to the parallel resonance circuit which has been described in the principle, and the mode of change of the electric current i is picked up from both terminals of the resistor R through the terminals A and B.

Figure 6:
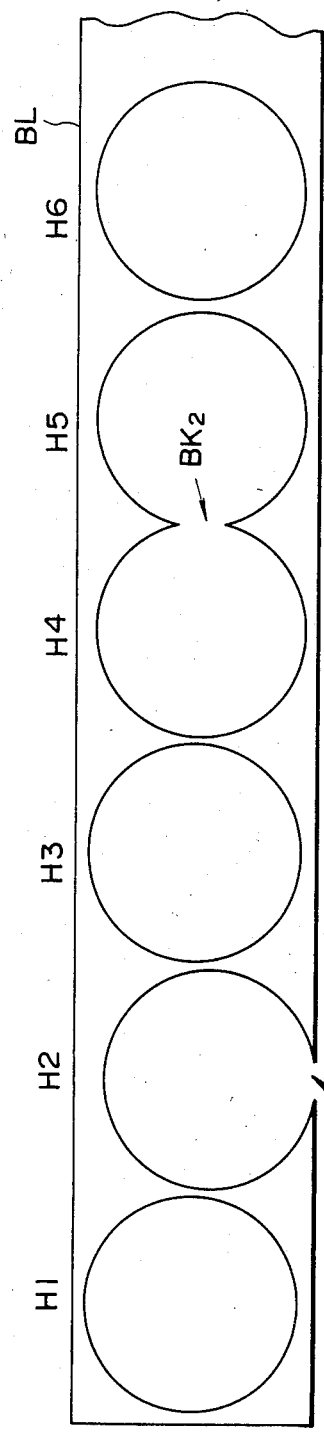
FIGS. 6(a) and 6(b) show an example of operation of the device of the embodiment illustrated in FIG. 5.
Figure 6:
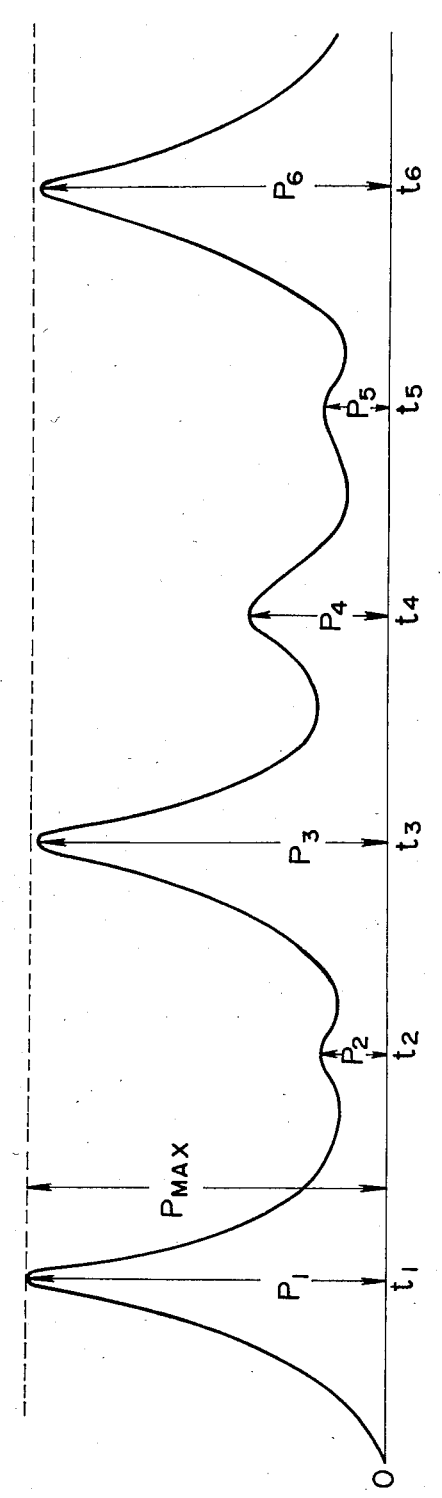

FIGS. 6(a) and 6(b) exhibit the mode of detection by the device of this embodiment with respect to the existence of the notch of the blank BL (FIG. 5), and the operation of the device of the embodiment will be described in the following by referring to the drawing, wherein it is assumed that two different kinds of the notches $BK_1$ and $BK_2$ as shown in FIG. 6(a) occur in the detected blank BL.

FIG. 6(b) exhibits the mode of change of the electric current i (That is the output waveform obtained between the terminals A and B after being shaped) outputted from the terminals A and B (FIG. 2), and the times $t_1$-$t_6$ are passing times of each punched portion $H_1$-$H_6$ of the blank BL shown in FIG. 6(a) with respect to the detecting head 100.

The operations of the device of the embodiment at each time $t_1$-$t_6$ are as follows:

at the time $t_1$: Since the punched portion $H_1$ is normal (closed loop), the mutual inductance exists between the punched portion $H_1$ and the coil 101 of the detecting head 100. With this existence, the resonating condition of the detecting head 100 is collapsed and the electric current i is increased.

at the time $t_2$: Since there is the notch $BK_1$ in the punched portion $H_2$, the secondary circuit (the punched portion $H_2$) becomes the open loop. Accordingly, the resonating condition of the detecting head 100 is retained, and the electric current i is decreased.

at the time $t_3$: Its condition is identical with the condition at the time $t_1$, and the electric current i is increased.

at the time $t_4$: Since there is the notch $BK_2$ in the punched portion $H_4$, the electric current i is decreased. By the way, in this case, the secondary circuit (the punched portion $H_4$) does not become the open loop completely on account of the equal balance with the punched portion $H_5$, but the influence of the mutual inductance existing between the punched portions $H_4$ and $H_5$ and the coil 101 of the detecting head 100 is extremely small, and the resonating condition in the detecting head 100 is almost retained. However, the electric current i is somewhat increased as compared with the condition at the time $t_2$.

at the time $t_5$: The relationship of the detecting head 100, dummy head 300, punched portions $H_5$ and $H_4$ becomes equivalent value with the relationship of FIG. 1(b) as described in the preceeding principle. Accordingly, the resonating condition of the detecting head 100 is retained, and the electric current i is decreased to a degree of the condition at the time $t_2$.

at the time $t_6$: Its condition is identical with the conditions at the time $t_1$ and $t_2$, and the electric current i is increased.

At the succeeding times not shown, the electric current based on the condition of the punched portion of the blank BL is outputted similar to the foregoing.

As described in the foregoing, the difference of the output electric currents between the case where the blank BL is normally punched and the case where the notch is produced is an enormous one (according to the actual measurement, the level difference of four times as a minimum), and it can be easily judged in a detected current treating device 400.

For example, as the methods of judgement, the following methods may be employed.

(1) When the blank BL is normally punched, one high level electric current is obtained always with respect to one punched portion. Accordingly, judgement is made as to whether or not the high level electric current by the predetermined number is obtained with respect to one blank.

(2) In one blank, a judgement is made as to whether or not the peak value ($P_1$, $P_2$, $P_3$, . . . shown in FIG. 6(b)) of the electric current level corresponding to each punched portion becomes more than ¼ of the maximum value ($P_{MAX}$ shown in FIG. 6(b)—the peak value $P_1$ in this example).

(3) A judgement is made as to whether or not the level of the output electric current exceeds a discriminating level after setting a proper discriminating level.

Also, in the detected electric current treating device 400, the discriminating signal to be properly formed under the foregoing judgement can be used as the emergency stop signal of the press or the various alarming signals therefore it has a broad usage.

In the foregoing device of the embodiment, an order of arrangement of the detecting head 100 and the dummy head 300 against the shifting direction of the blank BL is optional, and it may be, of course, possible to arrange so that the order of the arrangement positions shown in FIG. 5 become mutually opposite, or two dummy heads 300 may be prepared and the detecting head 100 be sandwiched in the shifting direction of the blank BL. In this case, more accurate judgement may be rendered against the occurrence of the notched $BK_2$ at the time when the punched portion $H_4$ approaches the detecting head 100 in the example of the blank BL shown in FIG. 6(a).

Also, in case the blank has more than a plurality of rows of the punched portions, a plurality of the detecting heads 100 and the dummy heads 300 may be prepared and they may be properly combined to obtain the results similar to the foregoing in simultaneous correspondence to the plurality of rows of the punched portions.

Furthermore, the construction of the detecting head 100 and the dummy head 300 is not, of course, limited to the embodiment shown in FIG. 5, and any constructions may be employed as long as the parallel resonance circuit is constituted.

Also, as the electric current supply means and the electric current extracting means to the detecting head 100, they are not limited to those described in the embodiment shown in FIG. 5, and in the detecting head 100, any means can be employed as long as the foregoing mode of detection can be obtained and the extraction can be made.

Now, the principle shown in FIG. 4 and the embodiment shown in FIG. 5, the description is provided only for making the detecting head 100 and the dummy head 300 as the parallel resonance circuit in view of easiness of simplification of the device, but it is, of course, possible to perform the blank checking by similarly using the series resonance circuit for the detecting head 100 and the dummy head 300, and in this case, when the notch is provided in the blank BL, the value of the extracted electric current i is increased, and if it is normal, the value of the extracted electric current i is decreased.

In the foregoing press punching defect detecting device, in order to perform the check of the blank BL in short time, the frequency of the electric current supplied to the detecting head 100 may be increased and the application to the high speed press is easy.

As described in the foregoing, according to the press punching defect detecting device and the device for performing the method, the defect on the end portion of the product punched by the press can be detected simply and accurately so that the reliability of the product is remarkably improved and at the same time, the economical control of the process without waste can be materialized.

What is claimed is:

1. A press punching defect detecting device, comprising:
    an electromagnetic sensor disposed at a passing position of a blank after a product is punched by a press for detecting electromagnetically the condition of an electric path formed by the circumference of a punched hole of the blank;
    an auxiliary sensor for detecting electromagnetically the condition of an adjacent electric path formed by the circumference of a punched hole adjacent to the circumference of a punched hole which said electromagnetic sensor monitors and for causing said electromagnetic sensor to output a signal representing that said electric path is an open loop when said electric path becomes a closed loop by the combination of the circumferences of the adjacent punched hole;
    a discriminating circuit for discriminating as to whether or not said electric path forms a closed loop on the basis of the output of the electromagnetic sensor,
    whereby the quality of the product punched by the press is discriminated;
    said electromagnetic sensor comprises a parallel resonance circuit, and an oscillator for providing an a-c current to said resonance circuit and a resistance for picking up current change flowing in the resonance circuit, and said auxiliary sensor is a parallel resonance circuit including an inductance which is coupled with the inductance of the resonance circuit of said electromagnetic sensor by a predetermined mutual inductance; and
    said parallel resonance circuits have mutually identical resonating condition, and a predetermined electric power is supplied only to the resonance circuit in said electromagnetic sensor.

2. A press punching defect detecting device according to the claim 1 in which said predetermined electric power is supplied in the condition where the parallel resonance circuit in said electromagnetic sensor is resonated when the electric path corresponding to the coil of the resonance circuit of said electromagnetic sensor forms an open loop.

3. A press punching defect detecting device according to the claim 2 in which said discriminating circuit discriminates as to whether the non-resonance output from the electromagnetic sensor is obtained by a predetermined number.

4. A press punching defect detecting device according to the claim 2 in which said discriminating circuit discriminates as to whether or not the level of the output electric current obtained from said electromagnetic sensor is more than $\frac{1}{4}$ with respect to the maximum level among the output electric currents.

5. A press punching defect detecting device according to the claim 2 in which said discriminating circuit discriminates as to whether the level of the output electric current obtained from said electromagnetic sensor exceeds an any present discriminating level.

* * * * *